United States Patent [19]

Blyakhman

[11] Patent Number: 5,591,811
[45] Date of Patent: Jan. 7, 1997

[54] 1-IMIDAZOLYLMETHYL-2-NAPHTHOLS AS CATALYSTS FOR CURING EPOXY RESINS

[75] Inventor: Yefim Blyakhman, Bronx, N.Y.

[73] Assignee: Ciba-Geigy Corporation, Tarrytown, N.Y.

[21] Appl. No.: 527,132

[22] Filed: Sep. 12, 1995

[51] Int. Cl.$^6$ .......................... C08G 59/00; C08G 65/08; C08G 65/14

[52] U.S. Cl. ..................... 525/504; 525/523; 528/94; 528/96; 528/361; 528/407

[58] Field of Search .................... 525/504, 523; 528/94, 361, 407, 96

[56] References Cited

U.S. PATENT DOCUMENTS

| | | | |
|---|---|---|---|
| 3,356,645 | 12/1967 | Warren | 260/47 |
| 3,638,007 | 1/1972 | Brooks | 235/184 |
| 3,751,471 | 8/1973 | Becker et al. | 528/107 |
| 3,792,016 | 2/1974 | Hill et al. | 260/47 |
| 4,101,514 | 7/1978 | Thom | 528/109 |
| 4,487,914 | 12/1984 | Barton | 528/92 |
| 5,001,212 | 3/1991 | Hammer et al. | 528/94 |

OTHER PUBLICATIONS

Farkas et al, Journal of Applied Polymer Science, vol. 12, pp. 159–168 (1968).
Lee et al, SPE Journal, vol. 16, p. 315 (1960).
Journal of Chemical Society, (1970) p. 1157–1161, F. Andreani et al.
Chemical Abstracts 100:23599, "Pigment Preparations and Their Use for Pigmenting of Intaglio Inks or Enamels".
Chemical Abstracts 96:201333, "Liquid, Stable Pigment Preparations and Their Use".

*Primary Examiner*—Frederick Krass
*Attorney, Agent, or Firm*—Michele A. Kovaleski

[57] ABSTRACT

1-Imidazolylmethyl-2-naphthols are effective catalysts and accelerators for curing epoxy resins, said naphthol compounds providing epoxy resin systems with prolonged room-temperature stability and fast curing at temperatures of 110°–150° C.

18 Claims, No Drawings

1-IMIDAZOLYLMETHYL-2-NAPHTHOLS AS CATALYSTS FOR CURING EPOXY RESINS

BACKGROUND OF THE INVENTION

The compound 1-imidazolylmethyl-2-naphthol is known. See, for example, *Journal of Chemical Society*, (1970), p. 1157–1161. However, use of said compound in conjunction with epoxy resins is not known.

Other types of imidazole catalysts and accelerators for use in conjunction with epoxy resins are known in the art and are widely used in many applications. Such imidazole compounds impart fast curing and a good balance of mechanical and thermal properties to the cured resins. See, for example, Lee and Nevill, *SPE Journal*, vol. 16, p. 315 (1960) and Farkas and Strohm, *Journal of Applied Polymer Science*, vol. 12, pp. 159–168 (1968).

The above-described known imidazoles, however, have certain drawbacks which limit their industrial use. For example, the known mixtures comprising polyepoxides and imidazoles (such as imidazole, 1-methylimidazole, 2-methylimidazole, 2-ethyl-4-methylimidazole, or 2-phenylimidazole) set up rapidly inasmuch as pot life at ambient temperature does not normally exceed 4–6 hours. Due to this short gel time, such compositions cannot readily be used in modern automated processes where a much greater stability is desirable, while at the same time, maintaining the ability of the resin to fast cure (i.e., a gel time of 0.5–5 minute) at the processing temperature.

Attempts have been made in the past to solve the above-described problem. For example, U.S. Pat. Nos. 3,356,645 and 5,001,212 teach a method of reducing the reactivity of imidazoles by formation of salts with organic and inorganic acids. But, in this case, only a slight increase in pot life is achieved, i.e., up to one week, which is still unacceptable for industrial standards.

Another approach is found in U.S. Pat. Nos. 3,638,007; 3,792,016; 4,101,514; and 4,487,914, which teach the formation of complexes of imidazoles with metal salts. However, in cases where a reasonable pot life is obtained in accordance therewith, it becomes necessary to increase the curing temperature to above 150° C., which temperature is undesirable for industrial applications. Further, contamination of cured resins with the metals used to form the complex commonly causes an increase in water absorption which in turn has a negative effect on dielectrical properties.

Therefore, the principal object of the instant invention is to provide an imidazole-type catalyst for use in conjunction with epoxy resin systems which substantially eliminates the disadvantages encountered with prior art materials and the method of use of such catalyst.

It is another object of the present invention to provide an imidazole/resin system where polymerization is initiated within 1–2 minutes and is complete in 3–15 minutes at a temperature of from 110°–150° C. in order to facilitate automated processing of the resin compositions.

It is a further object of the invention to provide such an imidazole/resin system without any substantial adverse impact on the thermal and mechanical properties thereof.

Various other objects and advantages of this invention will become apparent from the following description.

It has now surprisingly been discovered that addition of 1-imidazolylmethyl-substituted 2-naphthol compounds to epoxy resins in accordance with the present invention improves the storage stability of the resins while maintaining a fast curing time at moderate temperatures in the range of 110°–150° C. Therefore, use of the imidazole derivatives in accordance with the present invention provides an epoxy resin system which can be stored at room temperature for prolonged periods of time (i.e., a longer pot life) without adverse effects on curing time.

Furthermore, addition of the instant imidazolyl naphthol compounds to the resin system surprisingly improves mechanical properties and decreases water absorption with improved retention of modulus under hot/wet conditions. These improvements allow, for example, a longer service life of composites, structural parts and adhesives made from epoxy resins, which greatly decreases costs associated with repair and replacement.

SUMMARY OF THE INVENTION

The present invention relates to a storage-stable and fast curing epoxy resin and cured products made therefrom in which the curing catalyst is a 1-imidazolylmethyl-substituted-2-naphthol compound.

In general, the term "storage-stable" is to be understood in the practical sense for solid epoxy resins as being greater than or equal to six months storage stability at ambient temperature. For liquid epoxy resin compositions, "storage-stable" can be defined in the practical sense as having a pot life of two weeks or longer at ambient temperature. Stability can be measured by viscosity, melting point, gel time or reproducibility of cured resin properties after storage.

The term "fast curing" means, as to be generally understood herein, that curing is effectivated completely or nearly completely, in a few minutes or less at a moderate processing temperature, which is normally on the order of about 110°–150° C.

DETAILED DESCRIPTION OF THE INVENTION

More particularly, the instant invention pertains to a storage-stable, fast curing epoxy resin composition comprising A) an epoxy resin; and B) an amount in the range of from 2–25 parts by weight, per 100 parts of component (A), of a compound of formula (I)

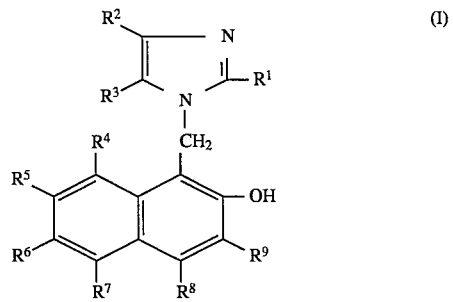

wherein $R^1$, $R^2$ and $R^3$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; aromatic or aliphatic acyl group of 3 to 12 carbon atoms; or alkyl or aryl of 3 to 12 carbon atoms containing a cyano group or halogen; and $R^4$, $R^5$, $R^6$, $R^7$, $R^8$ and $R^9$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; halogen; alkoxy of 1 to 12 carbon atoms; or hydroxy.

Applicable as epoxy resins in the present invention is any epoxy resin, including epoxy resins of the liquid type and of the solid type. For example, component (A) can be an epoxy resin selected from the group consisting of the glycidyl ethers of polyhydric phenols, of aliphatic or cycloaliphatic alcohols, of 4,4'-dihydroxydiphenyl sulfone, of dihydroxynaphthalene; of the condensation products of phenols or cresols with formaldehyde; the glycidyl ethers of halogenated mono-, di- or polynuclear phenols; glycidylated amines, aminophenols and amides; glycidylated polyacids; cycloaliphatic epoxy resins having epoxy groups attached to cyclohexane or cyclopentane rings; and mixtures thereof. Preparation of epoxy resins is well-known in the art.

Preferably, component (A) is an epoxy resin based on the diglycidyl ether of bisphenol A, the diglycidyl ether of bisphenol F, the diglycidyl ether of hydroquinone, of resorcinol, of catechol, of 2,5-dihydroxynaphthalene or of 9,9-bis(4-hydroxyphenyl)fluorene; the tetraglycidyl ether of 3,3,3',3'-tetramethyl-1,1'-spirobisindane-5,5',6,6'-tetraol; the tetraglycidyl derivatives of methylenedianiline, of m-phenylenediamine, of 1,4-di(α,α-dimethyl-3-methyl-4-aminobenzyl)benzene or of 3,3'-diethyl-4,4'-diaminodiphenylmethane; the triglycidyl derivatives of 4-aminophenol or 3-methyl-4-aminophenol; the diglyciyl derivative of aniline; di(2-glycidyloxy-1-naphthyl)methane, di(2,5-diglycidyloxy-1-naphthyl)methane or 2-glycidyl-oxy-1-naphthyl-2',5'diglycidyloxy-1'-naphthyl-methane.

Most preferably, component (A) is the epoxy resin of the diglycidyl ether of bisphenol A, the diglycidyl ether of bisphenol F, or the polyglycidyl ethers of the condensation products of phenols or cresols with formaldehyde.

Preferably, in component (B), $R^1$, $R^2$ and $R^3$ are each independently of the other hydrogen; alkyl of 1 to 12 carbon atoms; phenyl; or phenylalkyl of 7 to 15 carbon atoms optionally substituted by 1 to 3 alkyl groups of 1 to 4 carbon atoms. More preferably, $R^1$, $R^2$ and $R^3$ are each independently of the other hydrogen; alkyl of 1 to 8 carbon atoms; phenyl; or phenylalkyl of 7 to 15 carbon atoms optionally substituted by 1 to 3 alkyl groups of 1 to 4 carbon atoms. Even more preferably, $R^1$, $R^2$ and $R^3$ are each independently of the other hydrogen; alkyl of 1 to 4 carbon atoms; or phenyl. The most preferred compounds are 1-(2-methylimidazolylmethyl)-2-naphthol; 1-(2-ethyl-4-methylimidazolylmethyl)-2-naphthol; 1-(2-propylimidazolylmethyl)-2-naphthol and 1-(2-phenylimidazolylmethyl)-2-naphthol.

The 1-imidazolylmethyl-2-naphthols of the instant invention may be synthesized according to methods which are known in the art, for example, by condensation of 2-naphthols with imidazoles and formaldehyde according to the following reaction scheme:

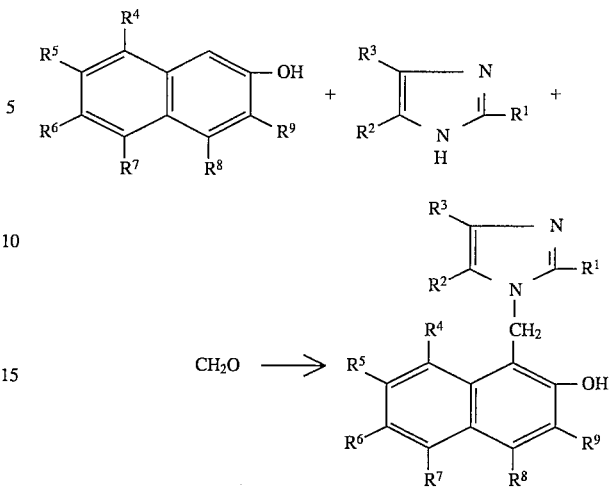

This route is preferred since the end product can be obtained in one step from starting materials which are commercially available. Such an analogous synthesis is described, for example, in *Vogel's Textbook of Practical Organic Chemistry*, Longman House, London, 1984.

Another possible preparative method for the 1-imidazolylmethyl-2-naphthols of the instant invention involves exchange of the dimethylamino group of a starting 1-dimethyl-aminomethyl-2-naphthol compound according to the following scheme:

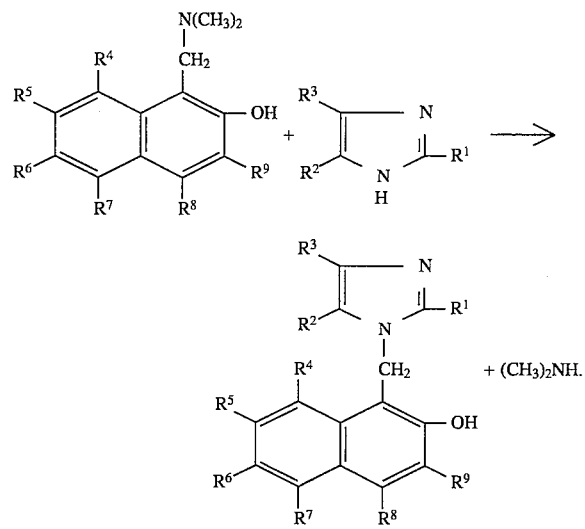

Such synthesis is described in J. Chem. Soc. (1970), discussed supra.

In accordance with the instant invention, the isolated 1-imidazolylmethyl-2-naphthol compound is added to and blended with an epoxy resin, such as described hereinabove, in about the range of 2 parts by weight to 25 parts by weight, per 100 pans of the epoxy resin. Preferably, the addition is made in about the range of 2 parts by weight to 15 parts by weight, and most preferably in about the range of 3 parts by weight to 6 parts by weight. If the epoxy resin is liquid, blending may be accomplished by simple agitation. If the epoxy resin is a solid at room temperature, blending may be accomplished by heating the epoxy resin to its softening point and melt-blending.

1-(2-Methylimidazolylmethyl)-2-naphthol has been found to be an especially effective catalyst for epoxy resins, said catalyst providing prolonged room-temperature pot-life, enhanced storage stability and fast curing at moderate temperatures of 110°–150° C. More specifically, said catalyst is particularly effective for solid epoxy resins having melting points (i.e., softening points) above 60° C. Said catalyst is especially suitable for epoxy resins made from bisphenol A and epoxy resins based on the condensation products of phenols and cresols with formaldehyde, said resins having a molecular weight of from about 1,000 to about 1,500.

For example, it has been discovered that 1-(2-methylimidazolylmethyl)-2-naphthol, which is insoluble in epoxy resins at room temperature, increases the pot life of catalyzed liquid epoxy resins to at least as great as three to four weeks when a dispersion thereof is formed. Likewise, when said catalyst is melt mixed into solid epoxy resins, storage stability of the resulting composition at room/temperature is at least 1.5 years.

Surprisingly, the insolubility of imidazolylmethyl-2-naphthols in epoxy resins does not interfere with fast curing at temperatures of 110° C. and above. Moreover, the cured resins have comparatively high glass transition temperature (Tg) and good mechanical properties with low water absorption and high retention of modulus under hot/wet conditions.

Therefore, use of 1-imidazolylmethyl-2-naphthol compounds in accordance with the present invention produces epoxy resin compositions which can be stored at room temperature without adverse effects to processing conditions, provides fast curing at moderate temperatures and results in materials with improved properties. These improvements are extremely desirable characteristics for processing due to better ability to handle the resins with no interference with curing time, which in turn, leads to reduced cost.

In accordance with the present invention, the 1-imidazolylmethyl-2-naphthol catalysts described herein are useful in any epoxy resin application, including use in adhesives, encapsulation and powder coatings. Techniques for preparing end products in such applications are well known to those skilled in the art.

The 1-imidazolylmethyl-2-naphthol compounds in accordance with the present invention may also be used as latent accelerators in conjunction with known curing agents for epoxy resins such as dicyandiamide, phenol- or cresolformaldehyde resins, aromatic polyamines, anhydrides, etc. That is, curing of an epoxy resin with known curing agents can be accelerated without reducing pot life or storage stability of the epoxy resin compositions.

The epoxy resin compositions in accordance with the instant invention may also further comprise any conventional additive normally associated with epoxy resin formulations such as accelerators, plasticizers, tougheners, flexibilizers, pigments, reinforcing agents, and/or fillers.

The following examples illustrate the preferred embodiments of the present invention and are intended for non-limitative purposes. In the examples, all parts are given by weight unless otherwise indicated.

Example 1

1-(2-Methylimidazolylmethyl)-2-naphthol

This example illustrates the preparation of a typical 2-imidazolylmethyl naphthol catalyst.

To a solution of 2-methylimidazole (82.1 g, 1 mole) and 2-naphthol (144.0 g, 1 mole) in isopropanol (400.0 g), formaline (37% aqueous solution, 1 mole of $CH_2O$) is added over a period of 30 minutes at room temperature. Thereafter, the reaction mixture is agitated for 30 minutes at room temperature, followed by agitation at 80°–84° C. for four hours. The mixture is then cooled and filtered. The filtrate is triturated and dried in vacuo at 60° C. The product (a white powder) is obtained in a yield of 92% with a melting point of 207° C., as determined by Differential Scanning Calorimetry (DSC).

Analysis: Calcd for $C_{15}H_{14}N_2O$: C, 75.6; H, 5.9; N, 11.8. Found: C, 75.5; H, 5.9; N, 11.6.

Example 2

1-(2-Ethyl-4-methylimidazolylmethyl)-2-naphthol

To a 35% solution of 2-ethyl-4-methylimidazole (110g, 1 mole) and 2-naphthol (144 g, 1 mole) in isopropanol, formaline (37% aqueous solution, 1 mole of $CH_2O$) is added over a period of 15 minutes at room temperature, followed by three hours of refluxing at 82°–84° C. The product (a white powder) is obtained in a yield of 85%, with a melting point of 166° C.

Analysis: Calcd for $C_{17}H_{18}N_2O$: C, 76.7; H, 6.8; N, 10.5. Found: C, 76.5; H, 6.9; N, 10.3.

Example 3

1-(2-phenylimidazolylmethyl)-2-naphthol

To a 30% solution of 2-phenylimidazole (144 g, 1 mole) and 2-naphthol (144 g, 1 mole) in isopropanol, formaline (37% aqueous solution, 1 mole of $CH_2O$) is added over a period of 30 minutes at room temperature, followed by six hours of refluxing at 82°–84° C. The product (270 g of a white powder) is obtained in a yield of 90%.

Analysis: Calcd for $C_{20}H_{16}N_2O$: C, 80.1; H, 5.3; N, 9.3. Found: C, 80.3; H, 5.5; N, 9.2.

Example 4

This example illustrates the preparation and curing of typical liquid epoxy resin composition in accordance with the present invention.

Liquid GY 6010 epoxy resin (100.0 g) (diglycidyl ether of bisphenol A from Ciba-Geigy Corporation, epoxy equivalent weight of 185–196) is mixed with the imidazolylmethyl-2-naphthol compound of Example 1 (5.0 g). The resultant mixture is folded on a two-roll mill at 20° C. to obtain a homogeneous dispersion, which dispersion is subsequently degassed, poured into an aluminum mold which is preheated to 130° C., and cured for 10 minutes at this temperature. The cured samples are tested for flexural modulus and strength in accordance with the test method ASTM D790. Dynamic mechanical analysis (DMA) is carried out with specimens having 3×12.5×30 mm in resonating doubleclamped beam mode at a heating rate of 10° C./min. The samples are tested for water absorption after 48 hours immersion in boiling water. The results are presented below in Table 1.

Comparative Example 5

Liquid GY 6010 epoxy resin (100.0 g) is mixed with N-methylimidazole (5.0 g). The mixture is cured and tested in accordance with the methods set forth in Example 4. The results are presented below in Table 1.

TABLE 1

Properties of Epoxy Resin GY 6010
Cured with 1-(2-methylimidazolylmethyl)-2-naphthol.
Comparative Example is same epoxy resin cured with
N-methylimidazole

| | Example 4 | Comparative Example 5 |
|---|---|---|
| Composition Pot Life at 25° C. | 3 weeks | 6 hours |
| Cured Resin $T_g$ (DMA), °C. | 152 | 156 |
| Water Absorption, % | 2.0 | 3.1 |
| (48 hours boiling water) | | |
| DMA Modulus, ksi | | |
| RT Dry | 411 | 449 |
| 80° C. Wet | 310 | 285 |
| Retention, % | 75 | 63 |
| 100° C. Wet | 289 | 262 |
| Retention, % | 70 | 58 |
| RT Flexural | | |
| Modulus, ksi | 370 | 385 |
| Strength, ksi | 14 | 14 |
| Strain, % | 5.1 | 5.1 |

As is evident from the above results, use of 1-(2-methylimidazolylmethyl)-2-naphthol as catalyst in an epoxy resin gives a much longer pot life (i.e., three weeks versus six hours), similar glass transition temperature (Tg) and similar mechanical properties, but with lower water absorption and better retention of modulus under hot/wet conditions.

Example 6

This example illustrates the preparation and curing of a typical solid epoxy resin composition in accordance with the present invention.

Solid epoxy resin GT 7072 (diglycidyl ether of bisphenol A from Ciba-Geigy Corporation, epoxy equivalent weight of 550–700) is mixed in powder form with 1-(2-methylimidazolylmethyl)-2-naphthol. The resulting mixture is roll-milled at 70°–75° C. for five minutes to obtain a homogeneous mixture in a form of white flakes.

Example 7

A homogeneous mixture of epoxy cresol novolac ECN 1299 (100 g) (polyglycidyl ether of o-cresol novolac from Ciba-Geigy Corporation, epoxy equivalent weight of 235) and 1-(2-methylimidazolylmethyl)-2-naphthol (5.0 g) is prepared in accordance with the method described in Example 6.

The samples of Examples 6 and 7 are tested by Differential Scanning Calorimetry (DSC) in isothermal mode on model DSC 2910, available from DuPont. The results are set forth below in Table 2.

TABLE 2

| Example | Curing Temperature °C. | Complete Curing Time, Min. Tested immediately after preparation | Tested after 18 months of storage at room temperature | Tested immediately after preparation | Tested after 18 months storage at room temperature |
|---|---|---|---|---|---|
| 6 | 120 | 15 | 14 | 131 | 131 |
| | 130 | 10 | 10 | 132 | 132 |
| | 140 | 5 | 5 | 132 | 132 |
| 7 | 130 | 5 | 5 | 195 | 194 |
| | 150 | 2.5 | 2.3 | 199 | 199 |

As is evident from the above data, the compositions of Examples 6 and 7 are storage stable at room temperature. It is particularly noteworthy that the uncured epoxy compositions in accordance with the instant invention show no change in reactivity after 18 months of storage as well as no change in Tg values after 18 months of storage for cured epoxy resin compositions in accordance with the present invention.

What is claimed is:

1. A storage-stable, fast curing epoxy resin composition comprising

A) an epoxy resin containing glycidyl ether groups and having an epoxy equivalent weight of 700 or less; and B) an amount in the range of from 2–25 parts by weight, per 100 parts of component (A), of a compound of formula (II)

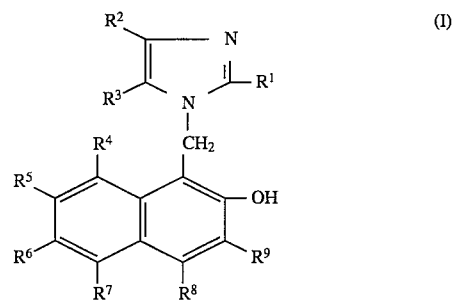

(I)

wherein $R^1$, $R^2$ and $R^3$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; aromatic or aliphatic acyl group of 3 to 12 carbon atoms; or alkyl or aryl of 3 to 12 carbon atoms containing a cyano group or halogen; and $R^4$, $R^5$, $R^6$, $R^7$, $R^8$ and $R^9$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; halogen; alkoxy of 1 to 12 carbon atoms; or hydroxy.

2. A storage-stable, fast curing epoxy resin composition according to claim 1 wherein, in the compound of formula (II), $R^1$, $R^2$ and $R^3$ are each independently of the other hydrogen; alkyl of 1 to 12 carbon atoms; phenyl; or phenylalkyl of 7 to 15 carbon atoms, or said phenylalkyl substituted by 1 to 3 alkyl groups of 1 to 4 carbon atoms.

3. A storage-stable, fast curing epoxy resin composition according to claim 2 wherein, in the compound of formula (II), $R^1$, $R^2$ and $R^3$ are each independently of the other hydrogen; alkyl of 1 to 12 carbon atoms; phenyl; or phenylalkyl of 7 to 15 carbon atoms, or said phenylalkyl substituted by 1 to 3 alkyl groups of 1 to 4 carbon atoms; and $R^4$–$R^9$ are each hydrogen.

4. A storage-stable, fast curing epoxy resin composition according to claim 2 wherein, in the compound of formula (II), $R^1$, $R^2$ and $R^3$ are each independently of the other hydrogen; alkyl of 1 to 8 carbon atoms; phenyl; or phenylalkyl of 7 to 15 carbon atoms, or said phenylalkyl substituted by 1 to 3 alkyl groups of 1 to 4 carbon atoms.

5. A storage-stable, fast curing epoxy resin composition according to claim 4 wherein, in the compound of formula (II), $R^1$, $R^2$ and $R^3$ are each independently of the other hydrogen; alkyl of 1 to 8 carbon atoms; phenyl; or phenylalkyl of 7 to 15 carbon atoms, or said phenylalkyl substituted by 1 to 3 alkyl groups of 1 to 4 carbon atoms; and $R^4$–$R^9$ are each hydrogen.

6. A storage-stable, fast curing epoxy resin composition according to claim 4 wherein, in the compound of formula (II), $R^1$, $R^2$ and $R^3$ are each independently of the other hydrogen; alkyl of 1 to 4 carbon atoms; or phenyl.

7. A storage-stable, fast curing epoxy resin composition according to claim 6 wherein, in the compound of formula (II), $R^1$, $R^2$ and $R^3$ are each independently of the other hydrogen; alkyl of 1 to 4 carbon atoms; or phenyl; and $R^4$–$R^9$ are each hydrogen.

8. A storage-stable, fast curing epoxy resin composition according to claim 6 wherein, in the compound of formula (II), $R^1$ is alkyl of 1–3 carbon atoms or phenyl; $R^2$ and $R^3$ are each independently of the other hydrogen or alkyl of 1–3 carbon atoms.

9. A storage-stable, fast curing epoxy resin composition according to claim 6 wherein, in the compound of formula (II), $R^1$ is alkyl of 1–3 carbon atoms or phenyl; $R^2$ and $R^3$ are each independently of the other hydrogen or alkyl of 1–3 carbon atoms; and $R^4$–$R^9$ are each hydrogen.

10. A storage-stable and fast curing epoxy resin composition according to claim 9, wherein component (B) is 1-(2-methylimidazolylmethyl)-2-naphthol.

11. A storage-stable and fast curing epoxy resin composition according to claim 9, wherein component (B) is 1-(2-ethyl-4-methylimidazolylmethyl)-2-naphtol.

12. A storage-stable and fast curing epoxy resin composition according to claim 9, wherein component (B) is 1-(2-propylimidazolylmethyl)-2-naphthol.

13. A storage-stable and fast curing epoxy resin composition according to claim 9, wherein component (B) is 1-(2-phenylimidazolylmethyl)-2-naphthol.

14. A storage-stable and fast curing epoxy resin composition according to claim 1 wherein component (A) is liquid at room temperature.

15. A storage-stable and fast curing epoxy resin composition according to claim 1 wherein component (A) is solid at room temperature.

16. A storage-stable and fast curing epoxy resin composition according to claim 1 further comprising an accelerator, plasticizer, toughener, flexibilizer, pigment, reinforcing agent filler or a further curing agent.

17. The cured resin product obtained after curing the composition of claim 1.

18. A method of preparing a storage-stable, fast-curing epoxy resin composition which cures at a temperature of from about 110°–150°, which method comprises adding to an epoxy resin, containing glycidyl ether groups and having an epoxy equivalent weight of 700 or less, from 2–25 parts by weight, per 100 parts of epoxy resin, of a compound of formula (I)

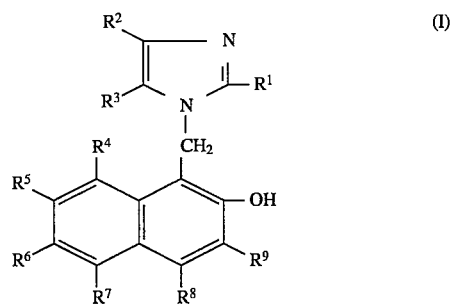

wherein $R^1$, $R^2$ and $R^3$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; aromatic or aliphatic acyl group of 3 to 12 carbon atoms; or alkyl or aryl of 3 to 12 carbon atoms containing a cyano group or halogen; and $R^4$, $R^5$, $R^6$, $R^7$, $R^8$ and $R^9$ are each independently of the other hydrogen; alkyl of 1 to 12 carbon atoms; cycloalkyl of 3 to 12 carbon atoms, or said cycloalkyl substituted by alkyl groups of 1 to 4 carbon atoms; cycloalkyl-alkyl of 4 to 20 carbon atoms, or said cycloalkyl-alkyl substituted by alkyl groups of 1 to 4 carbon atoms; aryl of 6 to 10 carbon atoms, or said aryl substituted by 1 to 3 alkyl groups of 1 to 4 carbon atoms; phenylalkyl of 7 to 15 carbon atoms, or said phenylalkyl substituted by 1 to 3 alkyl groups of 1 to 4 carbon atoms; alkenyl of 3 to 12 carbon atoms; alkynyl of 3 to 12 carbon atoms; halogen; alkoxy of 1 to 12 carbon atoms; or hydroxy.

* * * * *